(12) United States Patent
Lee et al.

(10) Patent No.: US 10,352,914 B2
(45) Date of Patent: Jul. 16, 2019

(54) P-TYPE ENVIRONMENT STIMULUS SENSOR

(71) Applicant: North Carolina State University, Raleigh, NC (US)

(72) Inventors: Bongmook Lee, Raleigh, NC (US); Veena Misra, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 204 days.

(21) Appl. No.: 15/427,663

(22) Filed: Feb. 8, 2017

(65) Prior Publication Data

US 2017/0227483 A1 Aug. 10, 2017

Related U.S. Application Data

(60) Provisional application No. 62/292,484, filed on Feb. 8, 2016.

(51) Int. Cl.
*G01N 33/00* (2006.01)
*G01N 27/12* (2006.01)
*G01N 27/02* (2006.01)

(52) U.S. Cl.
CPC ....... *G01N 33/0027* (2013.01); *G01N 27/127* (2013.01); *G01N 27/02* (2013.01)

(58) Field of Classification Search
CPC ........ G01N 27/00; G01N 27/02; G01N 27/04; G01N 27/12; G01N 27/125; G01N 27/127; G01N 27/62; G01N 33/00; G01N 33/0004; G01N 33/0006; G01N 33/0009; G01N 33/0027; G01N 33/0062; G01N 33/0067; G01N 33/0073; G01N 33/0075; G01N 17/00; G01N 17/006; G01N 17/02; G01N 22/00; G01N 2203/0641; G01N 24/008; G01N 31/00; G01R 27/06; G01R 31/2822; G01R 33/3232
See application file for complete search history.

(56) References Cited

U.S. PATENT DOCUMENTS

| | | | | |
|---|---|---|---|---|
| 5,623,212 A * | 4/1997 | Yamanaka | ........... | G01N 27/122 324/693 |
| 6,496,009 B2 * | 12/2002 | Kataoka | ............... | G01N 27/123 324/464 |
| 8,443,647 B1 * | 5/2013 | Kolmakov | ........... | G01N 27/127 324/601 |
| 9,453,814 B2 * | 9/2016 | Tran | ........................ | H01L 45/16 |
| 10,132,768 B2 * | 11/2018 | Shin | ..................... | G01N 27/125 |
| 10,161,062 B2 * | 12/2018 | Seebauer | ................ | C30B 31/08 |
| 2007/0086921 A1 * | 4/2007 | Visel | ..................... | B82Y 15/00 422/88 |
| 2009/0230979 A1 * | 9/2009 | Omote | ................... | B82Y 10/00 324/693 |
| 2011/0197657 A1 * | 8/2011 | Gole | .................... | G01N 27/021 73/31.05 |

(Continued)

*Primary Examiner* — Hoai-An D. Nguyen
(74) *Attorney, Agent, or Firm* — Kilpatrick Townsend & Stockton LLP

(57) ABSTRACT

An environmental stimulus sensor includes a substrate, a p-type material, and a conductive contact. In some aspects the conductive contact couples an electrode to the p-type material for supplying a current through the p-type material. The p-type material includes a nanotile structure for responding to an environmental stimulus by changing resistance.

20 Claims, 12 Drawing Sheets

(56) References Cited

U.S. PATENT DOCUMENTS

| | | | |
|---|---|---|---|
| 2015/0268184 A1* | 9/2015 | Gole | G01N 33/0027 73/31.06 |
| 2015/0300980 A1* | 10/2015 | Kim | H01L 21/02603 257/12 |
| 2016/0161461 A1* | 6/2016 | Gailius | G01N 33/0031 73/23.2 |
| 2016/0245830 A1* | 8/2016 | Mace | A61B 5/0075 |
| 2017/0200898 A1* | 7/2017 | Noh | G01N 33/497 |

* cited by examiner

P-TYPE ENVIRONMENT STIMULUS SENSOR

CROSS REFERENCE TO RELATED APPLICATIONS

This disclosure is related to and claims the benefit of priority of U.S. Provisional Application No. 62/292,484, titled "P-type Gas Sensors" and filed on Feb. 8, 2016, which is hereby incorporated in its entirety by this reference.

This invention was made with government support under grant number 1160483 awarded by the National Science Foundation. The government has certain rights to this invention.

TECHNICAL FIELD

The present disclosure relates generally to devices for detecting environmental stimuli. More specifically, but not by way of limitation, this disclosure relates to p-type environmental stimulus sensing devices.

BACKGROUND

Environmental stimuli can include gases and wireless signals (e.g., ambient light, UV light, or radio waves). Some environmental stimulus sensing devices may have different requirements based on different applications. For example, industrial applications may involve a sensor to detect gas concentrations in the high parts-per-million ("ppm"), whereas parts-per-billion ("ppb") precision may be needed for personal health monitoring. To obtain high precision, typical metal oxide sensors require high operating temperatures (e.g., greater than 200° C.). Some sensors include heating layers to obtain the high operating temperatures and can consume a high amount of power (e.g., tens of mWs), which can drain power sources and make wearing the sensors challenging. Furthermore, some sensors may be fabricated using chemical processes not suitable for large-scale fabrication.

SUMMARY

Aspects and examples are disclosed for a p-type environmental stimulus sensor.

In some aspects, an environmental stimulus sensor is disclosed. The environmental stimulus sensor can include a substrate, a p-type material, and a conductive contact. The p-type material can be in a nanotile structure on the substrate. The p-type material can respond to an environmental stimulus by changing resistance. The conductive contact can couple an electrode to the p-type material.

In additional or alternative aspects, a system is disclosed. The system can include an environmental stimulus sensor and a power source. The environmental stimulus sensor can detect an environmental stimulus. The environmental stimulus sensor can include a p-type material for responding to the environmental stimulus by changing resistance at room temperature. The power supply can be coupled to a metal contact of the environmental stimulus sensor for supplying a current through the p-type material.

In additional or alternative aspects, a method for fabricating an environmental stimulus sensor can be disclosed. The method can include applying a conductive contact to a substrate to form a sensor electrode. The method can further include heating a source material in a chamber such that a portion of the source material evaporates. The method can further include placing a sample that includes the substrate and the sensor electrode in the chamber downstream of the source material at a position that is heated to a lower temperature than a center of the chamber such that a p-type material condensates on the sample to form an active layer with a nanotile structure for detecting a stimulus in an environment.

These illustrative examples are mentioned not to limit or define the invention, but to aid understanding thereof. Other aspects, advantages, and features of the present invention will become apparent after review of the entire description and figures, including the following sections: Brief Description of the Figures, Detailed Description, and Claims.

DETAILED DESCRIPTION

Figure 1:
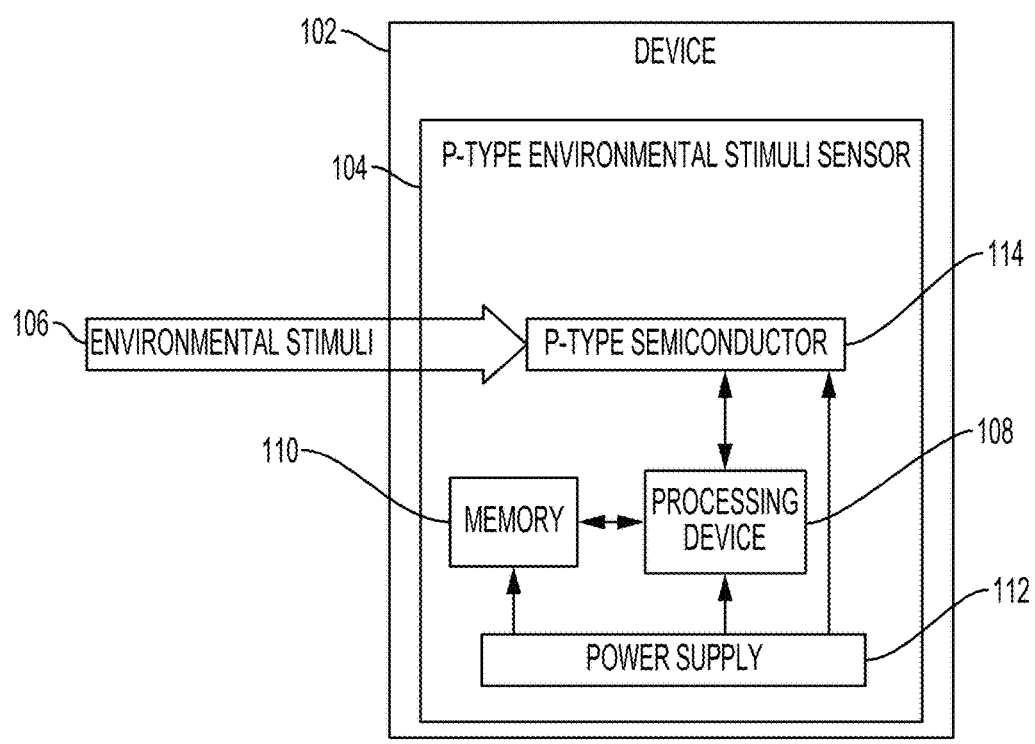
FIG. 1 is a block diagram of an example of a device with a p-type environmental stimulus sensor according to one aspect of the present disclosure.

Certain aspects and features of the present disclosure relate to a p-type environmental stimulus sensor. The p-type environmental stimulus sensor can include a p-type metal oxide semiconductor (e.g., SnO, CuO, Cu2O, or NiO) that can have a layer with p-type material (e.g., a layer with larger hole concentration than electron concentration and with a positive charge). The p-type material can be formed to have nanotiles that are structured in a non-uniform or quasi-non-uniform manner such that the surface area of the layer is higher than otherwise with a uniform structure. By having a high surface area and p-type material, the p-type environmental stimulus sensor can detect changes in an environmental stimulus (e.g., ozone, other gases, or ultraviolet light) without operating at a high temperature or a high power. For example, the p-type environmental stimulus sensor may be a gas sensor for operating at room temperature (e.g., approximately 20° C.) to detect a gas with a concentration in the low parts-per-billion ("ppb") with a capability of full recovery. Fully recovery can indicate that the p-type environmental stimulus sensor can include a characteristic (e.g., a resistance) with an initial state that changes in response to exposure the environmental stimulus and returns to the initial state in response to removal of the environmental stimulus. Furthermore, while operating at room temperature the p-type environmental stimulus sensor may have a low power consumption (e.g., approximately <10 μW) and may be integrated into a wearable device (e.g., a smart phone or a watch). The p-type environmental stimulus sensor may be manufactured using a process by which multiple p-type environmental stimulus sensors can be made at relatively low cost.

The Environmental Protection Agency ("EPA") identified several air pollutants (e.g., ozone and nitrogen dioxide) that people are exposed to in everyday life that can cause severe health effects, including illness, infection, and irritation. For example, exposure to ozone can cause several respiratory problems such as asthma. According to the National Ambient Air Quality Standards ("NAAQS"), the maximum eight-hour average ozone concentration is 75 ppb and the maximum one-hour average ozone concentration is 120 ppb. While the background ozone in the U.S. is estimated between 18 ppb to 36 ppb, the actual ozone level may vary near highways, urban areas, and indoors.

P-type environmental stimulus sensors may be able to measure a user's actual exposure to toxins such as ozone by being integrated into a portable device or a wearable device. Measuring a user's actual exposure may help correlate personal health with toxins in the user's environment. Some wearable devices are operated by batteries as a main power source and each component of the wearable devices may operate at relative low power consumption (in a range of microwatts) to avoid power consumption issues. A p-type environmental stimulus sensor according to certain examples may detect ozone at a low temperature with low power consumption. In some examples, a p-type environmental stimulus sensor can be coupled to a power generator or solar cell.

In some aspects, p-type environmental stimulus sensors may be fabricated using equipment that can allow the production to be scaled up to reduce production costs. For example, a p-type environmental stimulus sensor may use a standard six-inch or twelve-inch silicon ("Si") wafer as a substrate (e.g., a carrier substrate, which has a high electron mobility or hole mobility). Deposition techniques may permit an isolation layer to be deposited on the substrate. A metal contact can be applied to the isolation layer to form a sensor electrode.

A sample, including the substrate and the isolation layer with the metal contact, can be placed in a heating chamber (e.g., a furnace) with a source material such that the source material evaporates and causes a p-type material to condensate on the sample. Using this process, a functional p-type environmental stimulus sensor may be fabricated after a single run. Furthermore, multiple p-type environmental stimulus sensors can be fabricated on each Si wafer to result in high-volume fabrication.

A p-type material may include a larger hole concentration than electron concentration and have a positive charge. In some aspects, the p-type material may form an active layer with a nanotile structure as it condensates on the sample. In some examples, a nanotile structure can include multiple tiles (e.g., substantially rectangular blocks of the p-type material) that are between 1 nm and 1000 nm long. Each tile can extend from the substrate or the isolation layer at different angles such that the nanotile structure can have a high surface-area-to-volume ratio. An active layer can be a layer of a semiconductor device that can change resistivity to allow or block movement of charge carriers (e.g. holes or electrons). A large surface area may allow the p-type environmental stimulus sensor to detect small concentrations of an environmental stimulus, using low power and at room temperature. When exposed to the environmental stimulus, the p-type material may modulate its resistance. But, the p-type environmental stimulus sensor can be fully recoverable in that the p-type material can return to an original resistance once the p-type material is no longer exposed to the environmental stimulus. These features can allow the p-type environmental stimulus sensor to be effective in a portable or wearable device.

In some aspects, the p-type material may be used to detect a gas. For example, the p-type material may be used for detecting a concentration of ozone within the surrounding area. In additional or alternative aspects, the p-type material may be used in an optoelectronic device to detect light (e.g., ambient light or ultraviolet light). In additional or alternative aspects, the p-type material may be used in other electronic devices such as thin film diodes and transistors. In additional or alternative aspects, the p-type material can be used with n-type semiconductors to produce transparent or flexible electronics that can have a high performance.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

FIG. 1 is a block diagram of an example of a device 102 with a p-type environmental stimulus sensor 104 according to one aspect of the present disclosure. The p-type environmental stimulus sensor 104 may include a processing device 108, a memory 110, and a power supply 112. The p-type environmental stimulus sensor 104 also includes a p-type semiconductor 114. In some examples, the p-type semiconductor 114 includes a p-type metal oxide positioned with respect to a metal contact and a substrate. In additional or alternative examples, the p-type semiconductor 114 can include an isolation layer.

In some aspects, environmental stimulus 106 can include a concentration of a gas (e.g., ozone or nitrogen dioxide) within air that may flow through the device 102, through the p-type environmental stimulus sensor 104 and contact the p-type semiconductor 114. The p-type semiconductor 114 may respond to the concentration of the gas by modulating the resistance across the p-type metal oxide. The processing device 108 may determine the concentration of the gas based on the modulation of the resistance. In additional or alternative aspects, the environmental stimuli 106 can include a concentration of ultraviolet light or another wireless signal that propagates through a housing of the device 102 and p-type environmental stimulus sensor 104 to contact the p-type semiconductor 114. The p-type semiconductor 114 may respond to the concentration of the ultraviolet light by modulating the resistance across the p-type metal oxide. The processing device 108 may determine the concentration of the ultraviolet light based on the modulation of the resistance.

The processing device 108 can include any number of processors configured for executing program code stored in memory 110. Examples of the processing device 108 can include a microprocessor, an application-specific integrated circuit ("ASIC"), a field-programmable gate array ("FPGA"), or other suitable processor. In some aspects, the processing device 108 can be a dedicated processing device used to determine the concentration of a specific environmental stimulus (e.g., ozone). In other aspects, the processing device 108 can be used to determine the concentration of a variety of environmental stimuli including different gasses and different wireless signals.

The memory 110 can include, for example, one or more non-transitory computer-readable media that store program instructions executable by the processing device 108 to perform various operations. The operations may include measuring the resistance across a p-type metal oxide exposed to an environmental stimulus. The operations may further include determining a concentration of the environmental stimulus based on the resistance.

The power supply 112 may be coupled to the processing device 108, the memory 110, and the p-type semiconductor 114. The power supply 112 may apply a current that passes through the p-type semiconductor 114. As the current passes through the p-type semiconductor 114 a voltage drop may form across the p-type semiconductor. In some aspects, current from the power supply 112 may be applied, by the processing device 108, to the metal contacts of the p-type semiconductor 114. The processing device 108 may determine the resistance of the p-type metal oxide using the voltage drop and the current.

In some aspects, the processing device 108 may calculate the concentration of an environmental stimulus using the present resistance across the p-type metal oxide. In additional or alternative aspects, the p-type environmental stimulus sensor 104 may store data for subsequent calculations by the processing device 108. The p-type environmental stimulus sensor 104 may store data including resistance measurements, time of measurements, and geographic location of measurements. In additional or alternative aspects, a processing device and memory may be independent from the p-type environmental stimulus sensor 104. The p-type environmental stimulus sensor 104 may store data for later transfer to the independent processing device and memory.

In some aspects, the device 102 can be (or be integrated into) a wearable device. For example, the device 102 may couple to a band for being worn by a user, such as around a wrist of the user. In additional or alternative examples, the p-type semiconductor 114 may be integrated into a wearable device (e.g., the fabric of a shirt) and the processing device 108 may be integrated into a different wearable device (e.g., a watch) that is communicatively coupled to the p-type semiconductor 114. Both wearable devices may include a memory or only one may include a memory. The wearable device may provide the user with personal monitoring of exposure levels to environmental stimuli.

In additional or alternative aspects, the device 102 may include (or be integrated into) any portable device. For example, the device 102 may be integrated into a mobile computer or a smart phone. The portable device may allow for spatial monitoring of multiple users (e.g., workers in an area of a factory, or passengers in a car).

In other aspects, the p-type environmental stimulus sensor 104 may be an independent device. Although the p-type environmental stimulus sensor 104 is depicted as including both the processing device 108 and the memory 110, in other examples the p-type environmental stimulus sensor 104 may not include either or both of the processing device 108 or the memory 110.

Figure 2:
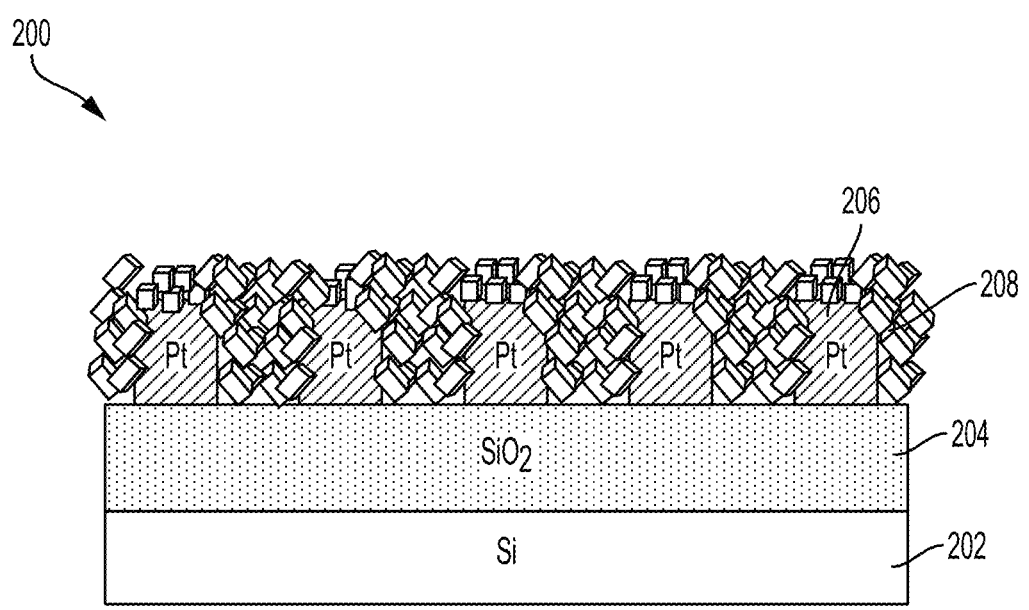
FIG. 2 is a cross-sectional diagram of an example of a p-type semiconductor for a p-type environmental stimulus sensor according to one aspect of the present disclosure.

FIG. 2 is a cross-sectional diagram of an example of a p-type semiconductor 200 for use in a p-type environmental stimulus sensor. The p-type semiconductor 200 is described as being used for detecting a gas (e.g., ozone), but other implementations are possible. For example, the p-type semiconductor 200 can be used for detecting a concentration of ultraviolet light. The p-type semiconductor 200 may include a substrate 202, an isolation layer 204, metal contacts 206, and p-type material 208.

Although the substrate 202 is illustrated as Si, any suitable semiconducting or insulating substrate materials (e.g., glass, quartz, or sapphire) may be used. The isolation layer 204 may be coupled to the substrate 202. In some aspects, the isolation layer 204 may be 300 nm thick. Although the isolation layer 204 is illustrated as silicon dioxide ("$SiO_2$"), any suitable insulating material may be used. In some aspects, a p-type semiconductor may not include an isolation layer by using a non-silicon substrate such as quartz.

The metal contacts 206 are coupled to the isolation layer to act as electrodes for measuring the resistance of the p-type material 208. In some aspects, the metal contacts 206 can be deposited using photolithography. Although the metal contacts 206 are illustrated as platinum ("Pt"), any suitable contact material (e.g., gold) may be used. In additional or alternative aspects, titanium ("Ti") or chrome ("Cr") may be used as an adhesive layer between the metal contacts 206 and the isolation layer 204.

The p-type material 208 may contact the metal contacts 206 and the isolation layer 204. In some aspects, the p-type material 208 includes tin (II) oxide ("SnO") in a nanotile structure. The resistance of the p-type material 208 may modulate based on contact with a gas and the temperature of the environment, as well as other factors. The nanotile structure can provide a high surface area, which can increase the exposure of the p-type material to the gas within the air. The high surface area can cause the p-type material 208 to respond, at room temperature, to a low concentration of a gas within the air (e.g., a concentration of 20 ppb) by modulating a resistance of the p-type material 208. The high surface area can cause the p-type material 208 to recover fully at room temperature when the target analyte is removed. The nanotile structures can include individual tiles that are conductively coupled to each other at or near the surface of the metal contacts 206 such that the conduction path between metal contacts 206 is minimized. A shorter conduction path between electrodes can improve the recovery of the p-type material 208.

In some aspects, current may be applied to the metal contacts 206, such that the current passes through the p-type material 208 and creates a voltage drop across the p-type material 208. The amount of the voltage drop and the amount of current can be used to calculate the resistance across the p-type material 208. In some aspects, the resistance can be used to determine the concentration of the gas.

Figure 3A:
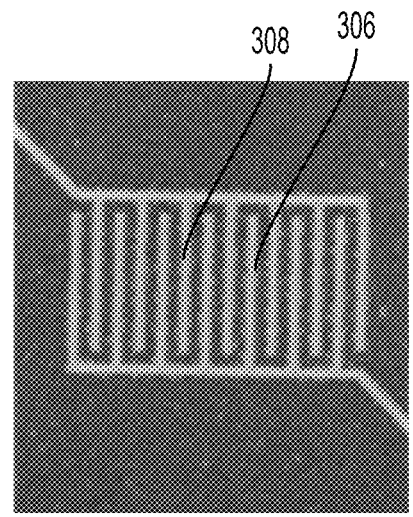
FIGS. 3A-C are magnified images of a top view of an example of a p-type environmental stimulus sensor according to one aspect of the present disclosure.
Figure 3B:
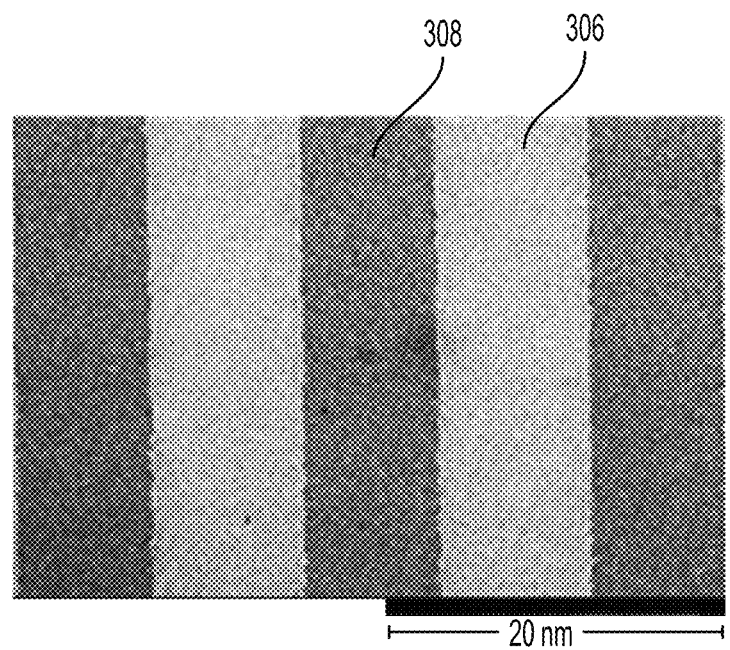
Figure 3C:
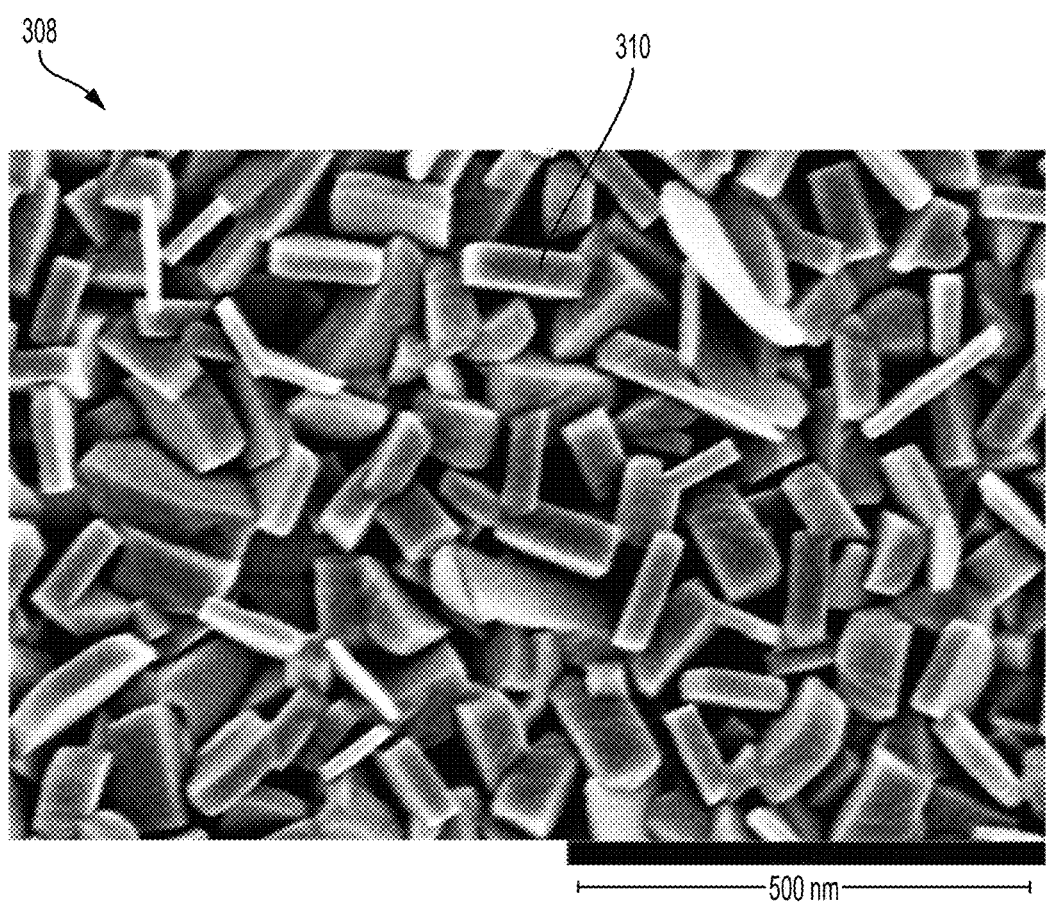

FIG. 3A-C are magnified images of a top view of an example of an environmental stimulus sensor. FIG. 3A-B depict a metal contact 306 coupled to a p-type metal oxide 308. FIG. 3C is a magnified image of an example of a surface of the p-type metal oxide 308 with a nanotile structure. In some aspects, the nanotile structure may include from 20 nm×40 nm to 60 nm×200 nm blocks 310. The non-uniform or non-linear structure of the blocks 310 can cause a high surface-area-to-volume ratio. The high surface-area-to-volume ratio may cause more contact between the p-type metal oxide and an environmental stimulus. For example, the high surface-area-to-volume ratio may provide more exposure of the p-type metal oxide to air, which can cause more contact between the p-type metal oxide and a gas within the air. The amount of contact between the p-type metal oxide and the environmental stimulus can determine the amount of modulation of the resistance of the p-type metal oxide for a specific concentration of the environmental stimulus. By increasing the modulation of the resistance for the specific concentration of the environmental stimulus, the p-type environmental stimulus sensor can have higher precision and operate at lower temperatures. Furthermore, the p-type environmental stimulus sensor may consume power at a low level. For example, the p-type environmental stimulus sensor may consume 10 μW to 200 μW of power while in operation.

Figure 4:
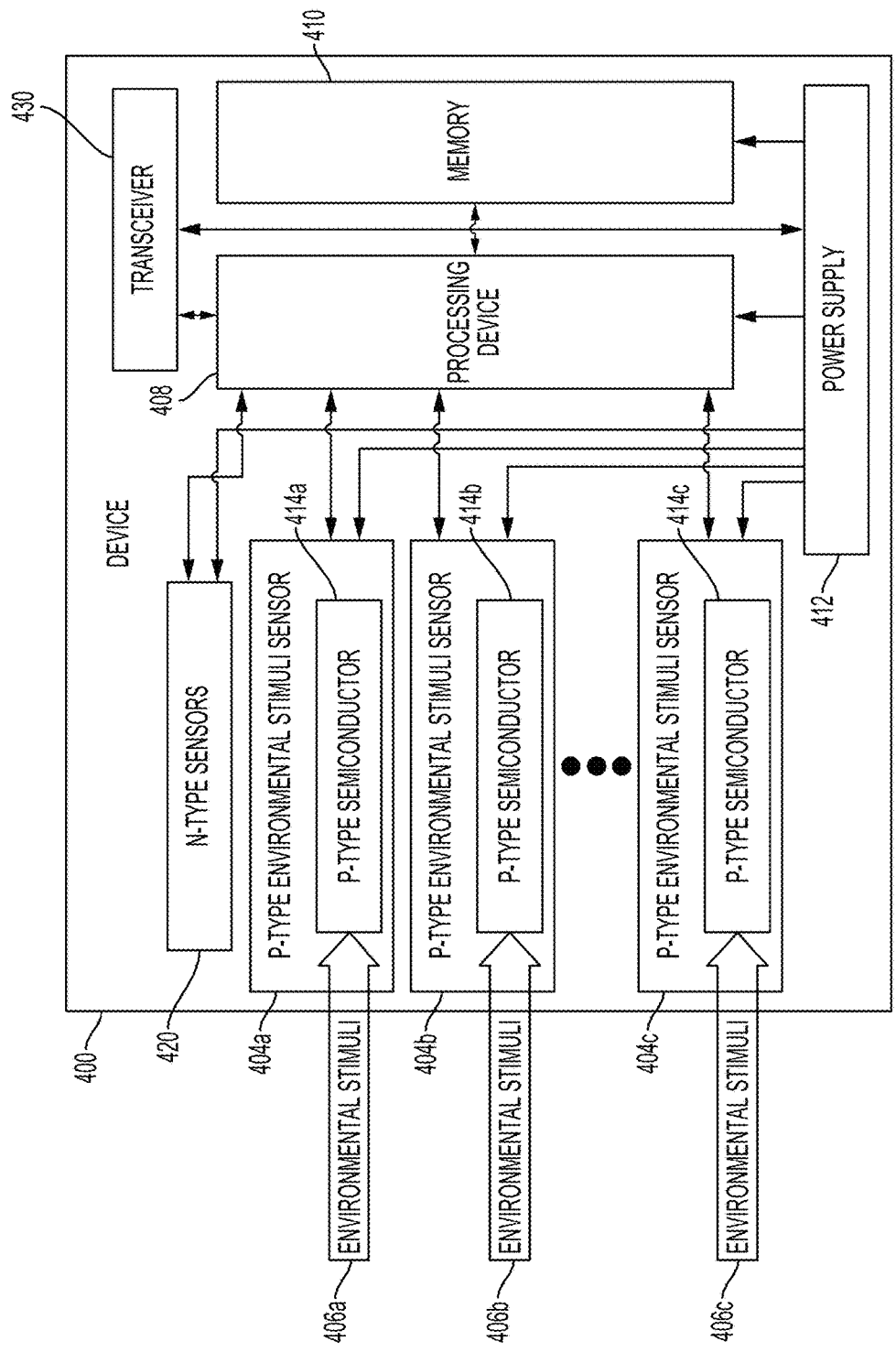
FIG. 4 is a block diagram of an example of a device with more than one p-type environmental stimulus sensor according to one aspect of the present disclosure.

FIG. 4 is a block diagram of an example of a device 400 that includes multiple p-type environmental stimulus sensors 404a-c and n-type sensors 420 to detect a variety of environmental stimuli 406a-c and other data in a variety of environmental conditions. For example, environmental stimuli 406a can include ozone, environmental stimuli 406b can include nitrogen dioxide, and environmental stimuli 406c can include ultraviolet light. The p-type environmental stimulus sensors 404a-c can each include one of the p-type semiconductors 414a-c, which can each respond to a different environmental stimulus. The p-type environmental stimulus sensors 404a-c and n-type sensors 420 can be communicatively coupled to a processing device 408 for determining concentrations of the environmental stimuli 406a-c based on responses of the p-type environmental stimulus sensors 404a-c and n-type sensors 420.

In some aspects, the processing device 408 can include similar features as the processing device 108 in FIG. 1. The processing device 408 can be communicatively couple to a memory 410, which can include code for causing the processing device to perform operations. The operations can include measuring a resistance across the p-type semiconductors 414a-c and determining values for different environmental stimuli 406a-c based on the resistance. A power supply 412 can be electrically coupled to the processing device 408, memory 410, n-type sensors 420, and the p-type environmental stimulus sensors 404a-c for providing power. In some aspects, the power supply 412 can include a battery or low-power component. In additional or alternative aspects, the power supply 412 can include a power generator (e.g., a solar cell).

The device 400 can also include a transceiver 430 communicatively coupled to the processing device 408 and electrically coupled to the power supply 412. The transceiver 430 can communicatively couple the device 400 with a mobile device (e.g., a mobile phone). In some examples, the transceiver 430 can transmit information about environmental stimuli 406a-c or other data determined by the processing device 408. In additional or alternative examples, the transceiver can receive information for use by the processing device 408 in detecting the environmental stimuli 406a-c.

Although the device 400 is depicted as including a single processing device 408, memory 410, and power supply 412, other implementations are possible. In some aspects, each of the p-type environmental stimulus sensors 404a-c can include a dedicated processing device. In some examples, the device 400 can include the p-type environmental stimulus sensor 104 in FIG. 1. In additional or alternative examples, device 400 can include (or be communicatively coupled to) device 100 in FIG. 1. In some aspects, device 400 can be a wearable device for measuring a variety of data about a user and the environmental conditions experienced by the user. In additional or alternative aspects, device 400 can be a portable device.

Figure 5:
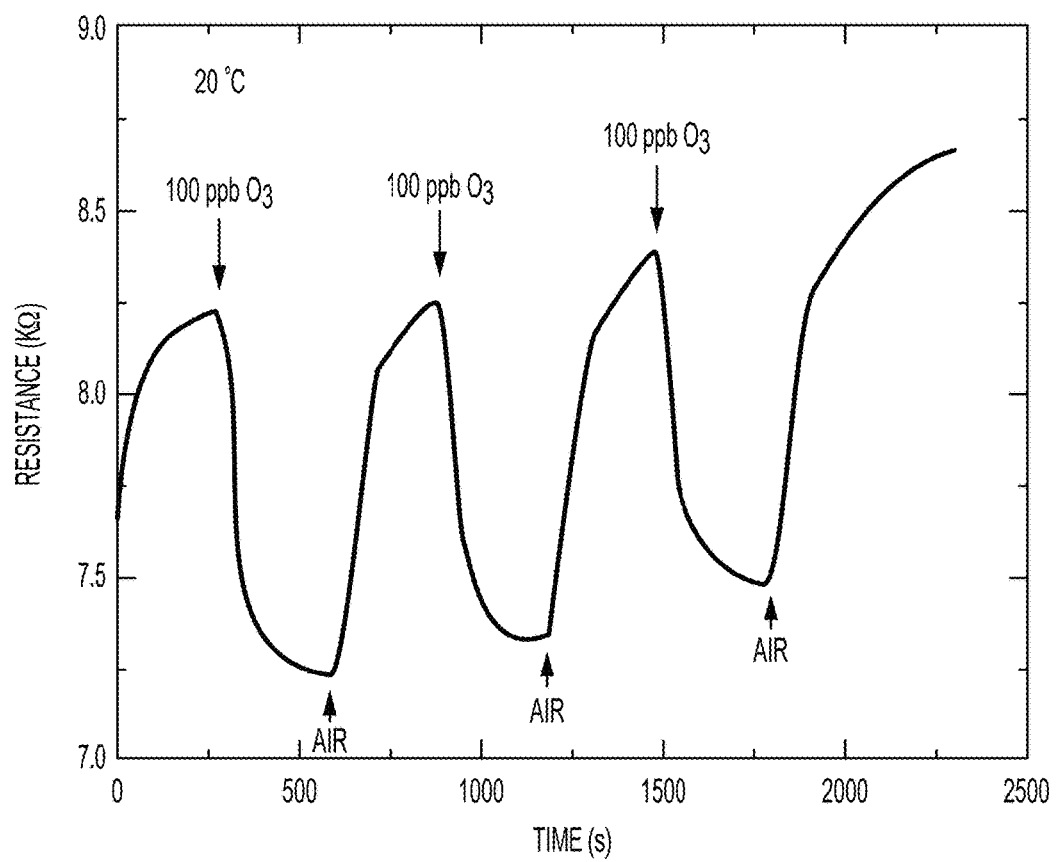
FIG. 5 is a graph of an example of measured resistances of a p-type environmental stimulus sensor in response to exposure to ozone according to one aspect of the present disclosure.

FIG. 5 is a graph of an example of measured resistances of a p-type environmental stimulus sensor in response to exposure to ozone. The graph includes three points in time in which ozone is introduced into the environment of the p-type environmental stimulus sensor. At room temperature, the resistance of the p-type environmental stimulus sensor drops by about 1 kΩ when exposed to a 100 ppb concentration of ozone. The graph also shows that the p-type environmental stimulus sensor can be fully recoverable. When ozone is no longer introduced to the environment of the p-type environmental stimulus sensor, the resistance returns to the original amount.

Figure 6:
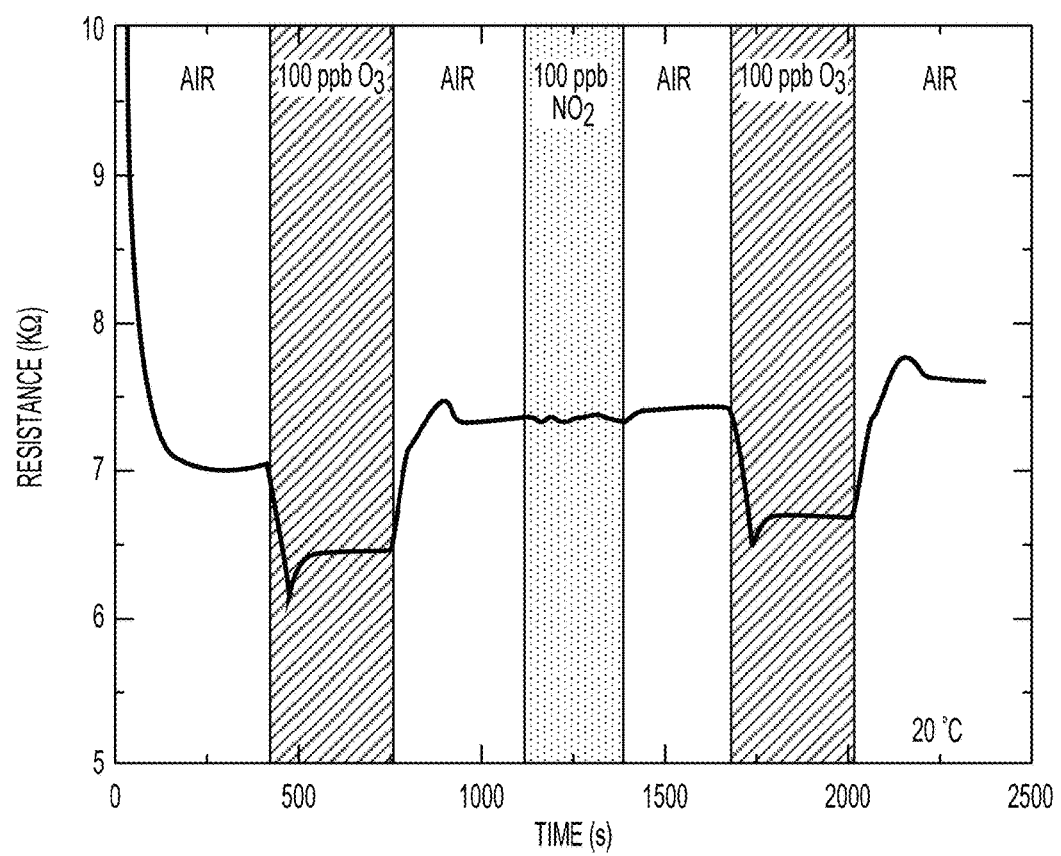
FIG. 6 is a graph of an example of measured resistances of a p-type environmental stimulus sensor in response to exposure to air with different concentrations of ozone and nitrogen dioxide according to one aspect of the present disclosure.

FIG. 6 is a graph of an example of measured resistances of a p-type material in a p-type environmental stimulus sensor exposed to different gasses. The graph shows seven time intervals, during which the p-type material is exposed to air with different concentrations of ozone and nitrogen dioxide. At room temperature, the resistance of the p-type material drops by about 1 kΩ when exposed to a 100 ppb concentration of ozone. Furthermore, the resistance returns to a constant resistance after the exposure to ozone, showing the p-type environmental stimulus sensor may be fully recoverable. Moreover, the resistance of the p-type environmental stimulus sensor is not modulated when exposed to nitrogen dioxide.

Figure 7:
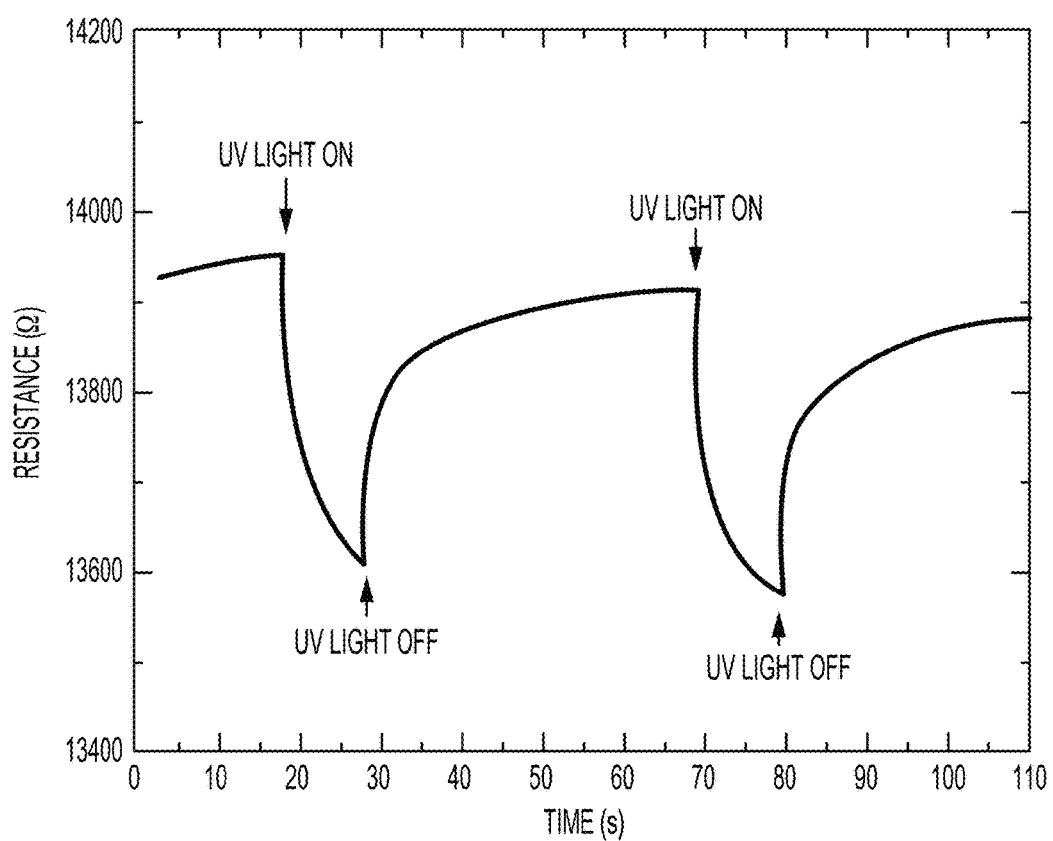
FIG. 7 is a graph of an example of measured resistances of a p-type environmental stimulus sensor in response to exposure to ultraviolet light according to one aspect of the present disclosure.

Although the resistance of the p-type materials in FIGS. 5 and 6 responds to ozone, other p-type environmental stimulus sensors may include a p-type material that responds to other gasses such as nitrogen dioxide or to other environmental stimuli such as light. For example, FIG. 7 is a graph of an example of measured resistances of a p-type material in a p-type environmental stimulus sensor for detecting ultraviolet light. The graph includes two points in time in which ultraviolet light is introduced into the environment of the p-type environmental stimulus sensor. At room temperature, the resistance of the p-type environmental stimulus sensor drops by about 400Ω when exposed to the ultraviolet light. The graph also shows that the p-type environmental stimulus sensor can be fully recoverable. When ultraviolet light is no longer introduced to the environment of the p-type environmental stimulus sensor, the resistance returns to the original amount.

In some aspects, the resistance of a p-type material may modulate more or less depending on the environmental temperature, the surface area of the p-type material, and the concentration of the gas, as well as other factors. Using a p-type material with a nanotile structure can increase the surface area of the p-type material and cause a modulation of the resistance when exposed to a low concentration of an environmental stimulus at a low temperature.

Figure 8:
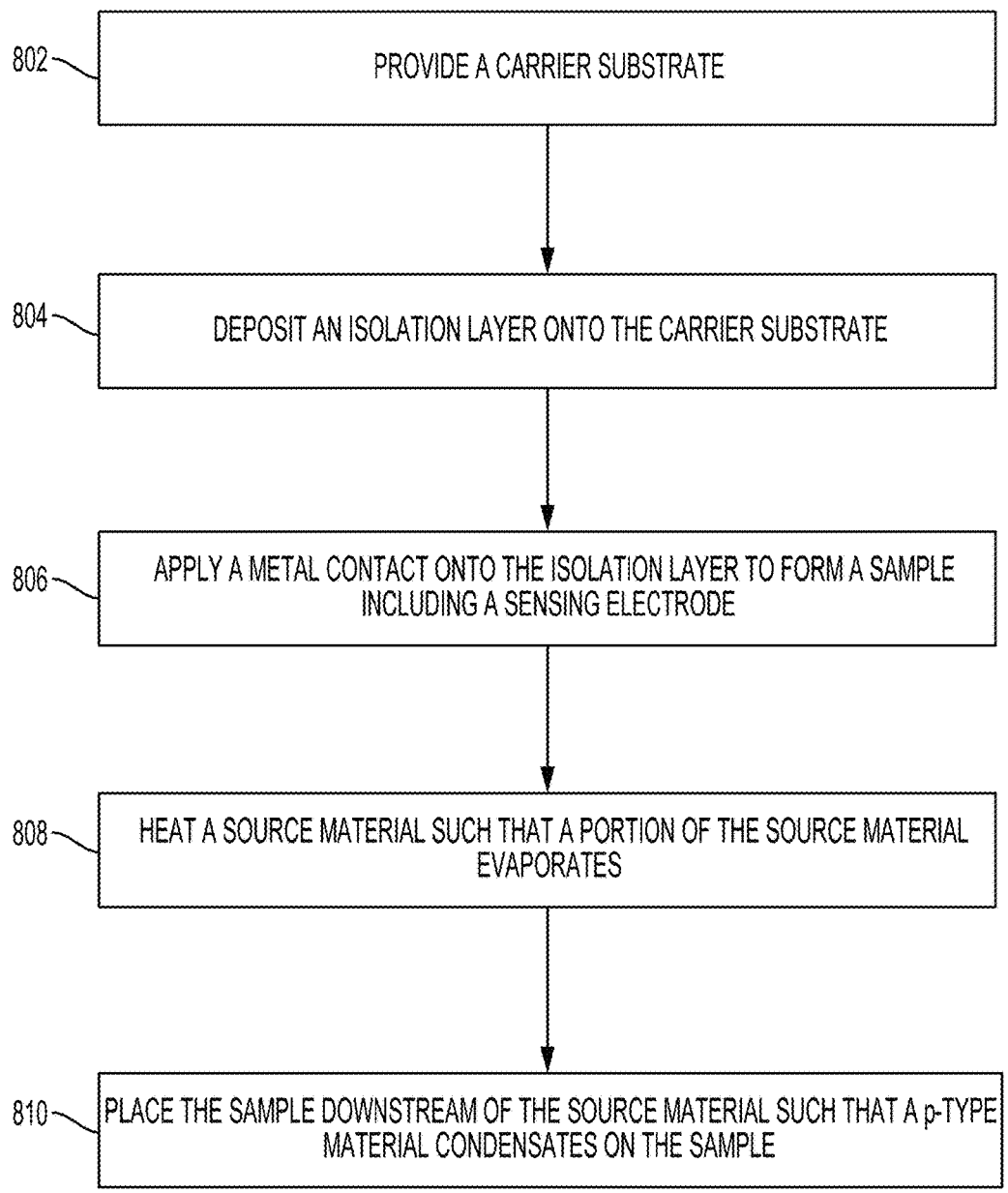
FIG. 8 is a flow chart of an example of a process for fabricating a p-type semiconductor for a p-type environmental stimulus sensor according to one aspect of the present disclosure.

FIG. 8 is a flow chart of an example of a process for fabricating a p-type semiconductor for a p-type environmental stimulus sensor. The process may create a functional sensor after a single run and the process may be scaled up to reduce production costs. The production costs may also be reduced as compared to the production of microelectromechanical system ("MEMS") type sensors due to the process having fewer steps.

In block 802, a carrier substrate is provided. In some aspects, the carrier substrate is a conducting layer made of Si. For example, the carrier substrate may be a 6-inch or 12-inch Si wafer. Multiple p-type environmental stimulus sensors can be fabricated on a single Si wafer to yield higher volume fabrication than a chemical fabrication process. In other aspects, the carrier substrate may be any suitable semiconducting or insulating layer.

In block 804, an isolation layer is deposited onto the carrier substrate. In some aspects, the isolation layer may be $SiO_2$ formed by thermal oxidation of a Si substrate. In additional or alternative aspects, the isolation layer can be formed by any suitable oxide deposited by any suitable process (e.g., chemical vapor deposition ("CVD"), physical vapor deposition ("PVD"), or atomic layer deposition ("ALD")) that blocks current between the substrate and the electrode.

In block 806, a metal contact is applied to the isolation layer to form a sample including a sensor electrode. The metal contact may be a platinum layer that is 100 nm to 200 nm thick with an adhesion layer that is 5 nm to 20 nm thick made of Ti deposited using an e-beam evaporation technique or a sputter deposition. In additional or alternative aspects, the metal contact may be gold or another conductive material. In some aspects, the metal contact may be applied after deposition of p-type materials. In additional or alternative aspects, the metal contact may be an electrical contact made from any suitable conducting material. Although electrical contacts are described as metal contacts, in other examples the electrical contacts can be non-metal contacts. Examples of materials from which non-metal contacts can be made include indium-tin-oxide and other transparent conducting oxides.

In block 808, source material (e.g., $SnO_2$ mixed with graphite) is heated such that a portion of the source material evaporates. In some aspects, heating the source material includes heating the source material in a portion of a chamber heated to at least 850° C. At temperatures of at least 850° C., a reduction process can occur to produce a p-type material from the source material (e.g., $SnO_2(s)+C(s)\rightarrow SnO(g)+CO(g)$). In some aspects, the pressure of the chamber can be modified to allow the source material to evaporate at a higher or lower temperature. In some example, the chamber can be heated to 900° C. with a base pressure of 40 to 80 mTorr. In additional or alternative examples, the chamber can be heated between 850° C. and 1000° C.

In block 810, the sample, including the carrier substrate, isolation layer, and metal contact, is placed downstream of the source material. The sample may be placed in a downstream portion of the chamber heated to a lower temperature than the portion where the source material was heated. For example, the sample may be placed in a downstream portion heated to 300° C. to 400° C. less than the portion where the source material was heated. Some of the evaporated source material can condensate on the sample to form a p-type nanotile structure. In some aspects, the condensation may occur over a long period of time (e.g., three hours to eight hours) with a constant flow of Argon or another inert gas through the chamber. In additional or alternative aspects, condensation may occur over a shorter period of time (e.g., thirty minutes to three hours) to produce a nanotile structure with different dimensions. In one example, the growth pressure can be 1.5 Torr with continuous Argon gas flow. In additional or alternative aspects, a three nm to five nm seed layer of the p-type material may be deposited using an ultra-high vacuum molecular beam epitaxy ("UHV-MBE") system prior to placing the sample downstream of the source material. In other aspects, sputtering or e-beam evaporator can be used to deposit Sn seed materials. The seed layer can promote the condensation of the p-type material and can reduce the production time.

The nanotile structure that is formed may be responsive to an environmental stimulus such as gas or light by modulating a resistance of the p-type material. In some aspects, the environmental stimulus may be ozone and the p-type material may have the precision to detect ozone at a concentration of 20 ppb in the environment at room temperature.

Figure 9:
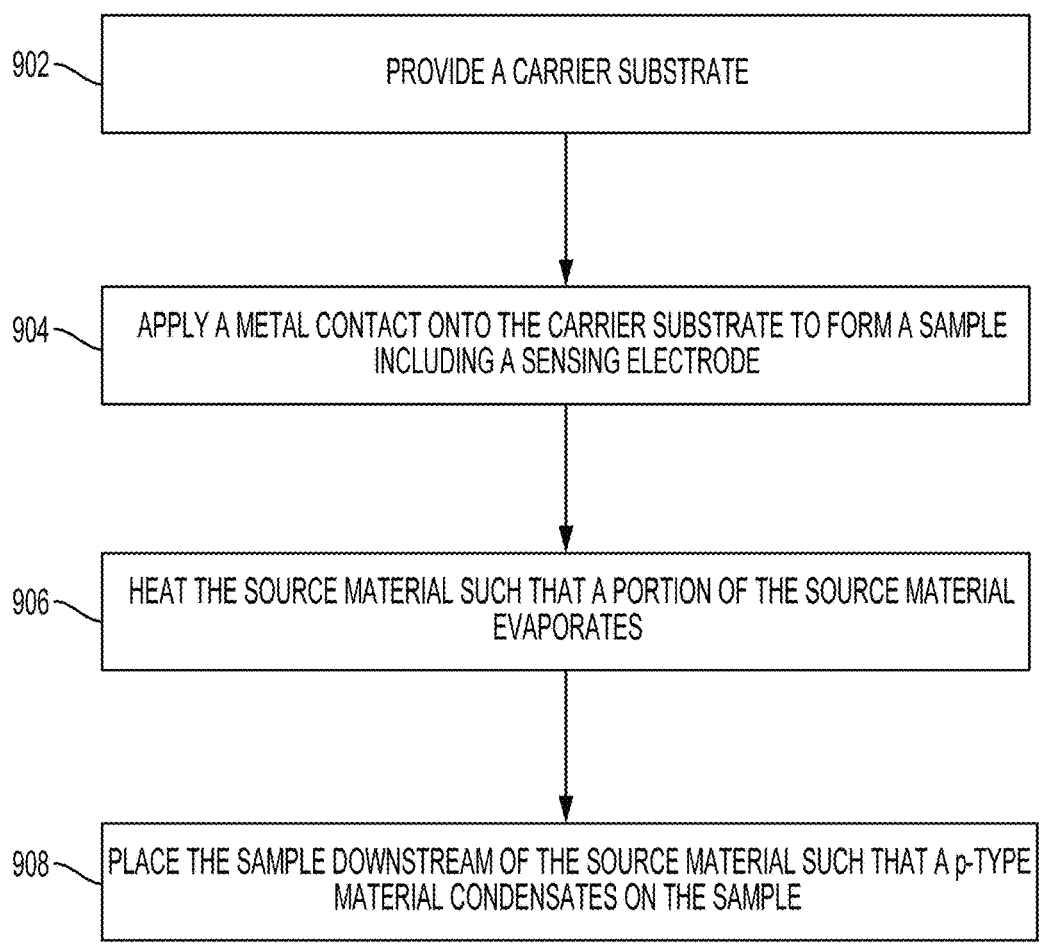
FIG. 9 is a flow chart of an example of a process for fabricating a p-type semiconductor with an insulating carrier substrate for a p-type environmental stimulus sensor according to one aspect of the present disclosure.

FIG. 9 is a flow chart of another example of a process for fabricating a p-type semiconductor for a p-type environmental stimulus sensor.

In block 902, a carrier substrate including an insulating material (e.g., glass, quartz, or sapphire) is provided. Using an insulating material as the carrier substrate can allow a sensor electrode to be formed directly on the carrier substrate without an isolation layer. As in block 802 of FIG. 8, the carrier substrate can include wafers and multiple p-type environmental stimulus sensors can be fabricated on a single wafer such that multiple environmental stimulus sensors can be formed during a single run of the process.

In block 904, a metal contact is applied to the carrier substrate to form a sample including a sensor electrode. The metal contact may be substantially similar to the metal contact described in block 806 of FIG. 8, but applied directly to the carrier substrate.

Blocks 906-908 can be substantially similar to blocks 808-810 in FIG. 8. In block 906, a source material can be heated such that a portion of the source material evaporates. In block 908, the sample including the carrier substrate and metal contacts are placed downstream of the source material such that a p-type metal material condensates on the sample to form an active layer. Some of the evaporated source material can condensate on the sample to form a p-type nanotile structure. The nanotile structure can have an amount of surface area that makes the p-type material responsive to environmental stimuli such as gas or light such that a resistance of the p-type material changes based on a concentration of the environmental stimulus. In some aspects, the environmental stimulus may be ozone and the p-type material may have the precision to detect ozone at a concentration of 20 ppb in the environment at room temperature.

Figure 10:
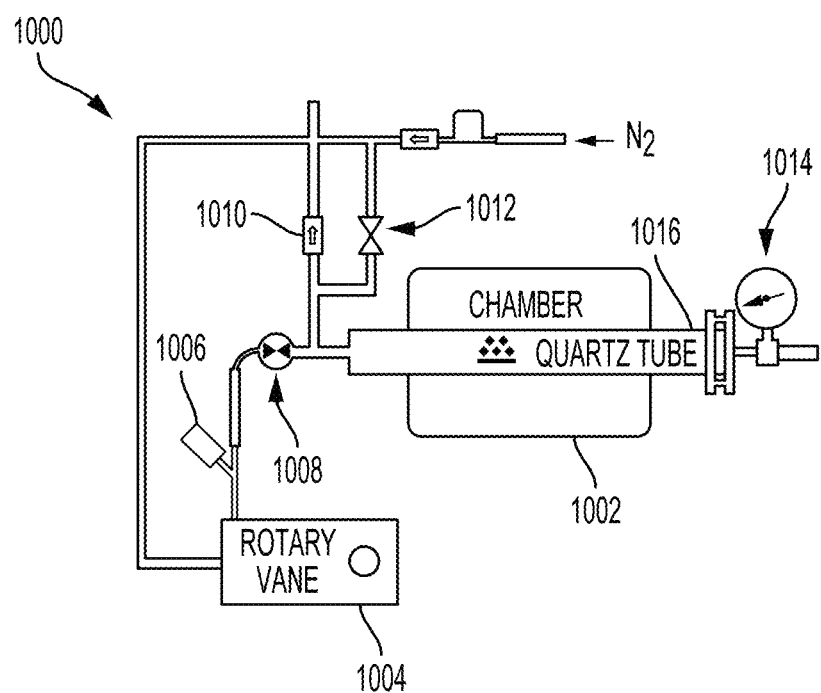
FIG. 10 is a schematic diagram of an example of an apparatus for performing part of the fabrication process in FIGS. 8-9 according to one aspect of the present disclosure.

FIG. 10 is a schematic diagram of an example of an apparatus 1000 for performing part of the fabrication process in FIG. 8-9. The apparatus 1000 includes a chamber 1002 (e.g., a furnace), rotary vane 1004, gate valve 1006, throttle valve 1008, safety valve 1010, atmospheric pressure valve 1012, and pressure gauge 1014. The chamber 1002 includes a tube 1016 that can be heated and pressurized. In some examples, the tube 1016 can be made of quartz or alumina. The rotary vane 1004 may be coupled to the gate valve 1006 such that when the gate valve 1006 is open, the rotary vane 1004 can pump the tube 1016. The tube 1016 may be coupled to a throttle valve 1008 to adjust the pressure within the tube 1016. The pressure gauge 1014 may be coupled to the tube 1016 and the pressure gauge 1014 can monitor the pressure within the tube 1016. The safety valve 1010 and atmospheric pressure valve 1012 may also be coupled to the downstream portion of the tube 1016 for releasing pressure.

Figure 11:
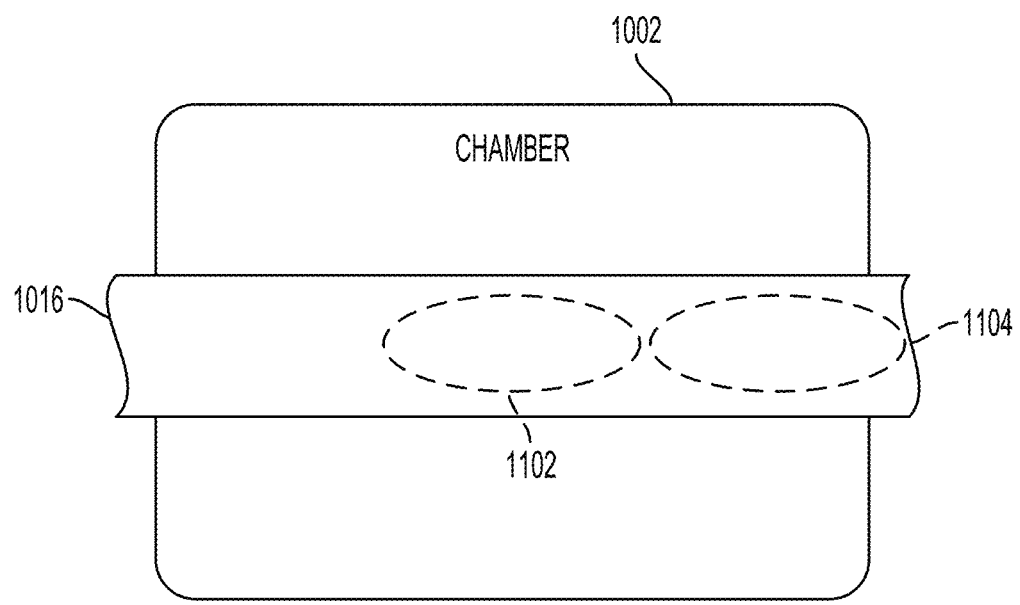
FIG. 11 is a schematic diagram of an example of the chamber from FIG. 10 with a center portion and a downstream portion according to one aspect of the present disclosure.

FIG. 11 is a schematic diagram of an example of the chamber 1002 from FIG. 10 with a center portion 1102 and a downstream portion 1104. Source material can be placed within the tube 1016 in a portion of the chamber 1002 with a temperature high enough to cause a portion of the source material to evaporate. In some aspects, the source material may be placed in the center portion 1102 of the chamber 1002 where the temperature may be the hottest. For example, the center portion 1102 may be at least 850° C. At this temperature, a portion of the source material may evaporate and flow towards the downstream portion 1104.

In some examples, a sample, including a carrier substrate, an isolation layer, and a metal contact, may be placed downstream from the source material. In some aspects, the sample may be placed in the downstream portion 1104, which may be heated to a lower temperature than the center portion 1102. For example, the downstream portion 1104 may be heated to 300° C. to 400° C. less than the center portion 1102 of the chamber 1002. At this reduced temperature, some of the evaporated source material may condensate on the sample to form a p-type nanotile structure.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. The examples of claims presented below are also not intended to be exhaustive or to limit claims emanating from the disclosure.

What is claimed is:

1. An environmental stimulus sensor comprising:
   a substrate;
   a p-type material on the substrate in a structure including multiple tiles of the p-type material extending from the substrate or an isolation layer at different angles, the p-type material being configured for responding to an environmental stimulus by changing resistance; and
   a conductive contact for coupling an electrode to the p-type material.

2. The environmental stimulus sensor of claim 1, wherein:
   the conductive contact is configured to be applied to the substrate to form a sensor electrode;
   a source material is configured to be heated in a chamber such that a portion of the source material evaporates; and
   a sample that includes the substrate and the sensor electrode configured to be placed in the chamber downstream of the source material at a position that is heated to a lower temperature than a center of the chamber such that the p-type material condensates on the sample to form an active layer with the structure.

3. The environmental stimulus sensor of claim 1, further comprising
   a processing device conductively coupled to the p-type material;
   a memory communicatively coupled to the processing device for storing instructions that are executable by the processing device for causing the processing device to:
      measure the resistance across the p-type material; and
      determine a concentration of the environmental stimulus at room temperature based on the resistance measured across the p-type material; and
   a power source coupled to the conductive contact of the environmental stimulus sensor for supplying the current through the p-type material.

4. The environmental stimulus sensor of claim 1, wherein the p-type material is configured to (i) have a first resistance in a room temperature environment in response to a first concentration of ozone detected by the environmental stimulus sensor, (ii) have a second resistance in the room temperature environment in response to a second concentration of ozone detected by the environmental stimulus sensor and that is between 20 and 100 ppb different from the first concentration of ozone, and (iii) return to the first resistance in response to the environmental stimulus sensor detecting the first concentration of ozone in the room temperature environment.

5. The environmental stimulus sensor of claim 1, wherein the substrate is silicon, the environmental stimulus sensor further comprising the isolation layer positioned between the substrate and the conductive contact, wherein the p-type material is on the isolation layer.

6. The environmental stimulus sensor of claim 1, wherein the substrate comprises an insulating material and the p-type material comprises at least one of SnO, CuO, Cu2O, or NiO for responding to the environmental stimulus in an environment of the environmental stimulus sensor.

7. The environmental stimulus sensor of claim 1, wherein the conductive contact is a metal contact comprising a platinum layer that is between 100 nm and 200 nm thick.

8. A system comprising:
   an environmental stimulus sensor configured for detecting an environmental stimulus, the environmental stimulus sensor comprising a p-type material for responding to the environmental stimulus by changing resistance at room temperature, the p-type material including multiple tiles at different angles relative to the environmental stimulus sensor; and
   a power source coupled to at least one metal contact of the environmental stimulus sensor for supplying a current through the p-type material.

9. The system of claim 8, wherein the environmental stimulus sensor further comprises:
   a conductive contact configured for coupling an electrode to the p-type material; and
   a substrate, the p-type material being on the substrate.

10. The system of claim 9, wherein:
    the conductive contact is configured to be applied to the substrate to form a sensor electrode;
    a source material configured to be heated in a chamber such that a portion of the source material evaporates; and
    a sample that includes the substrate and the sensor electrode configured to be placed in the chamber downstream of the source material at a position that is heated to a lower temperature than a center of the chamber such that the p-type material condensates on the sample to form an active layer.

11. The system of claim 9, wherein the environmental stimulus sensor and the power supply form a wearable device or a portable device for monitoring an amount of exposure of a user to the environmental stimulus.

12. The system of claim 9, further comprising:
    a processing device configured for communicatively coupling to the environmental stimulus sensor; and
    a memory configured for communicatively coupling to the processing device for storing instructions that are executable by the processing device for causing the processing device to:
       measure the resistance across the p-type material; and determine a concentration of the environmental stimulus based on the resistance.

13. The system of claim 12, wherein the instructions are executable for causing the processing device to detect a change of at least 20 ppb in the concentration of the environmental stimulus in a room temperature environment.

14. The system of claim 12, the system further comprising a transceiver configured for communicatively coupling to a mobile device for transmitting a signal to the mobile device that is usable for displaying the concentration of the environmental stimulus.

15. The system of claim 9, wherein the p-type material comprises at least one of SnO, CuO, Cu2O, or NiO configured for responding to a plurality of different types of environmental stimuli.

16. The system of claim 9, wherein the environmental stimulus sensor is a plurality of environmental stimulus sensors configured for detecting more than one environmental stimulus.

17. A method comprising:
   applying a conductive contact to a substrate to form a sensor electrode;
   heating a source material in a chamber such that a portion of the source material evaporates; and
   placing a sample that includes the substrate and the sensor electrode in the chamber downstream of the source material at a position that is heated to a lower temperature than a center of the chamber such that a p-type material condensates on the sample to form an active layer with a structure including multiple tiles of the p-type material at different angles relative to the sample for detecting a stimulus in an environment.

18. The method of claim 17, wherein placing the sample that includes the substrate and the sensor electrode in the chamber further comprises forming the active layer for responding to the stimulus in the environment at room temperature by changing resistance, the method further comprising coupling a power supply to the conductive contact for supplying a current through the p-type material.

19. The method of claim 17, wherein the substrate is silicon, wherein applying the conductive contact to the substrate further comprises:
   depositing an isolation layer on the substrate; and
   applying the conductive contact on the substrate to form the sensor electrode.

20. The method of claim 17, wherein heating the source material includes placing the source material in the center of the chamber, wherein the center of the chamber is heated to between 850° C. and 1000° C., and wherein the position is heated to at least 300° C. less than the center.

* * * * *

UNITED STATES PATENT AND TRADEMARK OFFICE
CERTIFICATE OF CORRECTION

PATENT NO. : 10,352,914 B2
APPLICATION NO. : 15/427663
DATED : July 16, 2019
INVENTOR(S) : Bongmook Lee and Veena Misra Page 1 of 1

It is certified that error appears in the above-identified patent and that said Letters Patent is hereby corrected as shown below:

On the Title Page

Item (54) and in the Specification, Column 1, Lines 1-2 in "Title", delete "ENVIRONMENT" and insert -- ENVIRONMENTAL --, therefor.

Signed and Sealed this
First Day of October, 2019

Andrei Iancu
*Director of the United States Patent and Trademark Office*